US006462228B1

(12) United States Patent
Dams

(10) Patent No.: US 6,462,228 B1
(45) Date of Patent: Oct. 8, 2002

(54) PROCESS FOR PREPARATION OF FLUORINATED SULFINATES

(75) Inventor: Rudolf J. Dams, Antwerp (BE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/582,121

(22) PCT Filed: Dec. 22, 1997

(86) PCT No.: PCT/US97/23749

§ 371 (c)(1),
(2), (4) Date: Sep. 25, 2000

(87) PCT Pub. No.: WO99/32429

PCT Pub. Date: Jul. 1, 1999

(51) Int. Cl.⁷ .............................................. C07C 205/00
(52) U.S. Cl. ..................................................... 562/125
(58) Field of Search ......................................... 562/125

(56) References Cited

U.S. PATENT DOCUMENTS

| | | |
|---|---|---|
| 2,666,797 A | 1/1954 | Husted et al. |
| 2,732,398 A | 1/1956 | Brice et al. |
| 2,803,615 A | 8/1957 | Ahlbrecht et al. |
| 2,803,656 A | 8/1957 | Ahlbrecht et al. |
| 3,346,612 A | 10/1967 | Hansen |
| 3,420,877 A | 1/1969 | Pavlik |
| 3,528,954 A | 9/1970 | Carlson |
| 3,616,371 A | 10/1971 | Ukihaski et al. |
| 3,635,926 A | 1/1972 | Gresham et al. |
| 3,900,372 A | 8/1975 | Childs et al. |
| 4,024,178 A | 5/1977 | Landucci |
| 4,029,868 A | 6/1977 | Carlson ........................ 526/247 |
| 4,043,965 A | 8/1977 | Dickson ................... 526/245 X |
| 4,046,944 A | 9/1977 | Mueller et al. .............. 428/262 |
| 4,123,602 A | 10/1978 | Ukihashi et al. ........... 526/20 X |
| 4,158,678 A | 6/1979 | Tatemoto et al. ........ 204/159 X |
| 4,243,770 A | 1/1981 | Tatemoto et al. ............. 525/331 |
| 4,499,249 A | 2/1985 | Nakagawa et al. .......... 526/206 |
| 4,558,141 A | 12/1985 | Squire .......................... 549/455 |
| RE32,199 E | 7/1986 | Carlson |
| 4,714,756 A | 12/1987 | Buckmaster .................. 528/481 |
| 4,791,166 A | 12/1988 | Saukaitis ...................... 524/544 |
| 4,791,167 A | 12/1988 | Saukaitis ...................... 524/544 |
| 4,946,936 A | 8/1990 | Moggi et al. ................. 528/392 |
| 4,948,844 A | 8/1990 | Nakahara et al. ............ 525/356 |
| 5,132,028 A | 7/1992 | Nagase et al. ............... 252/806 |
| 5,182,342 A | 1/1993 | Feiring et al. ............... 526/240 |
| 5,182,343 A | 1/1993 | Ono et al. ...................... 560/27 |
| 5,276,175 A | 1/1994 | Dams et al. .................. 526/222 |
| 5,285,002 A | 2/1994 | Grootaert ..................... 526/222 |
| 5,308,511 A | 5/1994 | Coppens et al. .............. 252/8.6 |
| 5,378,782 A | 1/1995 | Grootaert ..................... 526/255 |
| 5,475,070 A | 12/1995 | Ashizawa et al. ........... 526/246 |
| 5,516,578 A | 5/1996 | Coppens ...................... 428/260 |
| 5,532,310 A | 7/1996 | Grenfell et al. .............. 524/263 |
| 5,536,304 A | 7/1996 | Coppens et al. ............ 252/8.57 |
| 5,639,837 A | 6/1997 | Farnham et al. ............. 526/222 |
| 5,859,288 A * | 1/1999 | Forat et al. .................. 562/113 |
| 6,111,136 A * | 8/2000 | Marzouk et al. ............. 562/113 |
| 6,365,769 B1 * | 4/2002 | Behr et al. ................... 560/147 |

FOREIGN PATENT DOCUMENTS

| | | |
|---|---|---|
| DE | 1294949 | 5/1969 |
| EP | 077 998 | 5/1983 |
| EP | 336 607 | 10/1989 |
| EP | 383 310 | 8/1990 |
| EP | 526 976 A1 | 2/1993 |
| EP | 648 887 | 4/1995 |
| EP | 656 440 | 6/1995 |
| EP | 756 033 | 1/1997 |
| FR | 2 287 432 | 5/1976 |
| GB | 2 274 462 A | 7/1994 |
| WO | WO 93/24586 | 12/1993 |
| WO | WO 94/07937 | 4/1994 |
| WO | WO 97/02300 | 1/1997 |
| WO | WO 97/28229 | 8/1997 |
| WO | WO 99/16809 | 4/1999 |
| WO | WO 99/32439 | 7/1999 |
| WO | WO 99/35176 | 7/1999 |

OTHER PUBLICATIONS

"The Alkali Metals", *Comprehensive Inorganic Chemistry*, M.C. Sneed and R.C. Brasted, vol. Six, pp. 61–64, D. Van Nostrand Company, Inc., New York (1957).

"A Simple Synthesis of Tetraalkylammonium Salts with Functional Anions," *Justus Liebigs Ann. Chem.*, H. Kobler et al, pp. 1937–1945 (1978).

"Organic Fluoropolymers," W. Gerhartz, et al. Ed., D.P. Carlson and W. Schmiegel, *Ullmann's Encyclopedia of Industrial Chemistry*, 5ᵗʰ Edition, vol. A11, pp. 393–429, VCH Verlagsgesellschaft GmbH, Weinheim (1988).

"Poly(phenylene Ether) to Radical Polymerization," *Encyclopedia of Polymer Science and Engineering*, H. Mark et al., vol. 13, pp. 709–718, Ed John Wiley & Sons, New York (1985).

"Petroleum Products, Lubricants, and Fossil Fuels," *Annual Book of ASTM Standards*, Section 5, Test Method D56—97a, pp. 1–5 (1998) (Test Method D56—97a is current version of Test Method D56–87).

Test Method—118–1989, *AATCC Technical Manual*, vol. 67, pp. 194–195 (1992). (Test Method 118–1989 is a current version of Test Method 118–1983).

(List continued on next page.)

*Primary Examiner*—Deborah C. Lambkin
(74) *Attorney, Agent, or Firm*—Robert H. Jordan

(57) ABSTRACT

A process for preparation of a fluorinated sulfinate product by reacting a mixture comprising: (1) water; (2) dehalogenating and sulfinating reagent: and (3) fluoroaliphatic sulfonyl fluoride represented by the formula: $R_f-[SO_2F]_n$; and (4) at least one of the material selected from the group consisting of: (i) fluorinated surfactant, or (ii) organic cosolvent comprising, as the major component by weight of the organic solvent, alcohol having a boiling point of less than 110° C. at 760 torr; by heating the reaction mixture to a temperature between about 50° C. and 100° C. until the desired product yield is achieved. Also provided is a process of using the fluorinated sulfinate product as an initiation system for a free radical polymerization process, such as that used to prepare fluoropolymers.

21 Claims, No Drawings

OTHER PUBLICATIONS

Test Method 22, *AATC Technical Manual*, vol. 67, pp. 70–71 (1992).

"Studies on Sulfinatodehalogenation, IV. The Sulfinatodebromination of Primary Perfluoroalkyl Bromides and Perfluoroalkylene α, ω–Dibromides," *Acta Chimica Sinica*, Bing–Nan Huang,, Bing–Huang Wang, Wei Wang, Wei–Yuan Huang (1986).

"Studies on Sulfinatodehalogenation, VIII. Sodium Dithionite–Initiated Perfluoroalkyl Radical Addition on Double Bond," *Acta Chimica Sinica*, Wei–Yuan Huang, Wei Wang, Bing–Nan Huang, No. 2, (1986).

"A Simple Synthesis of Tetraalkylammonium Salts with Functional Anions," Liebigs Ann Chem, Heinz Kobler, Ruldolf Munz, Al Gasser, Gerhard Simchem, University Stuttgart, *Liebigs Ann. Chem.*, pp. 1937–1945, Chemie, Ltd., (1978).

"A Simple Synthesis of Tetraalkylammonium Salts with Functional Anions," *Liebigs Ann Chem*, Heinz Kobler, Ruldolf Munz, Al Gasser, Gerhard Simchem, University Stuttgart, Liebigs Ann. Chem., pp. 1937–1945, Chemie, Ltd., (1978).

Abstract for Chinese patent 1072407.
Abstract for German patent 1294949.
Abstract for French patent 2287432.
Abstract for Japanese patent 63235334.
Abstract for Japanese patent 03017106.
Abstract for Japanese patent 1151293.
Derwent abstract for Japanese patent 60152585.

"Organofluorine Compounds and Their Applications," H.C. Fielding, R.E., Society of Chemical Industry, R.E. Banks, Ed., London, p. 214 (1979).

"Reaction of Perfluoroalkanesulfinates with Allyl and Propargyl Halides. A Conveniet Synthesis of 3–(Perfluoroalkyl)prop–1–enes and 3–(Perfluoroalkyl)allenes," Chang–Ming Hu, Feng–Ling Qing and Wei–Yuan Huang, *Journal of Organic Chemistry*, 56, pp. 2801–2804, (1991).

Photoxidation of Perhalofluorosulfinates. A Simple and Effective Method for the Synthesis of Perhalofluorocarboxylic Acids and Their Esters from the Corresponding Sulfonyl Fluorides, Chang–Ming Hu, Ze–Qi Xu, and Wei–Yuan Huang, *Journal of Fluorine Chemistry*, 42, pp. 145–148 (1989).

"Reaction of Perhalofluoroalkyl Sulfinates With One–Electronc Transfer Oxidants. A Facile Method for the Synthesis of Perhalofluorocarboxylic Acids," Chang–Ming Hu, Ze–Qi Xu and Wei–Yuang Huang, *Journal of Fluorine Chemistry*, 49, pp. 433–437 (1990).

Perfluoroalkylation Initiated with Sodium Dithionite and Related Reagent Systems, Wei–Yuan Huang, *Journal of Fluorine Chemistry*, 58, pp. 1–8 (1992).

"The Reaction of Perfluoroalkanesulfinates. IX. Perfluoroalkylation of Pyridine and its Derivatives with Sodium Perfluoroalkanesulfinates," Wei–Yuan Huang, Jin–Tao Liu, Juan Li, *Journal of FLuorine Chemistry*, 71, pp. 51–54 (1995).

"Studies on Deiodo–Sulfination Part. II. The Reactions of Perfluoroalkanesulfinates with Halogen and Halogen Acids and a New Method for the Synthesis of Perfluorsulfonic Acid," Wei–Yuan Huang, Bing–Nan Huang and ChangMing Hu, *Journal of Fluorine Chemistry*, 23, pp. 229–240 (1983).

"Acrylamide Polymers," H. Mark et al., *Encyclopedia of Polymer Science & Engineering*, $2^{nd}$ Ed., vol. 1, pp. 169–211, John Wiley & Sons, New York (1985).

"Acrylic and Methacrylic Acid Polymers," H. Mark et al., *Encyclopedia of Polymer Science & Engineering*, $2^{nd}$ Ed., vol. 1, pp. 211–234, John Wiley & Sons, New York (1985).

"Acrylic and Methacrylic Ester Polymers," H. Mark et al., *Encyclopedia of Polymer Science & Engineering*, $2^{nd}$ Ed vol. 1, pp. 234–299, John Wiley & Sons, New York (1985).

"Maleic and Fumaric Polymers," H. Mark et al., *Encyclopedia of Polymer Science & Engineering,* $2^{nd}$ Ed., vol. 9, pp. 225–294, John Wiley & Sons, New York (1985).

"Vinyl Ester Polymers," H. Mark et al., *Encyclopedia of Polymer Science & Engineering*, $2^{nd}$ Ed., vol. 17, pp. 393–468, John Wiley & Sons, New York (1985).

"Vinylidene Chloride Polymers," H. Mark et al., *Encyclopedia of Polymer Science & Engineering*, $2^{nd}$ Ed., vol. 17, pp. 492–531, John Wiley & Sons, New York (1985).

"The Alkali Metals," M. Cannon Sneed and Robert C. Brasted, Comprehensive Organic Chemistry, vol. 6, pp. 61–64, D. Van Nostrand Company, Inc., Princeton, New Jersey.

"Single Electron–Transfer Process in Perfluoroalkyl Halides Reactions," Claude Wakselman, *Journal of Fluorine Chemistry*, 59, pp. 367–378 (1992).

"Studies on Sulfinatodehalogenation. XXIX. The Sulfinatodehalogenation of Primary Polyfluoroalkyl Iodies and Bromides by Sodium Disulfite," Wu Fan–Hong and Huang Bing–Nan, *Journal of Fluorine Chemistry*, 67, pp. 233–234 (1994).

* cited by examiner

PROCESS FOR PREPARATION OF FLUORINATED SULFINATES

This application is a 371 of PCT/US97/23749 Dec. 22, 1997.

FIELD OF THE INVENTION

The present invention relates to a method for preparing fluorinated sulfinates and the use of the sulfinates obtained from the method as polymerization initiators, and particularly as initiators for the free radical polymerization of fluorinated monomers.

BACKGROUND OF THE INVENTION

Fluorinated sulfinates have utility as reactive intermediates and precursors for fluorochemical sulfonyl halides and perhalofluorocarboxylic acids and their esters. They are also useful as initiators in free radical polymerization reactions.

For example, U.S. Pat. No. 5,285,002 describes the use of fluoroalkyl sulfinates as a source of fluoroalkyl radicals in aqueous emulsion polymerizations. The resulting polymers contain a high level of perfluoroalkyl end groups, and when fluoroalkyl disulfinates are utilized, fluoroalkyl moieties are incorporated into the polymer backbone thereby yielding fluoropolymers with specific microstructural fragments which are derived from the fluoroalkyl disulfinate.

U.S. Pat. No. 5,639,837 discloses a process in which fluorine containing olefins are polymerized using an initiation system which is a combination of a fluoroaliphatic sulfinate or sulfinic acid and chlorate, bromate or hypochlorite ions. The resulting polymer contains fewer deleterious end groups and is more stable and/or easier to process.

Methods for the synthesis of fluorochemical sulfinates and their use as intermediates have been widely reported in the literature. For example, perfluoroalkane sulfinates can be prepared from the corresponding perfluoroalkanehalides via a dehalogenation and sulfination reaction, as reported in C. M. Hu, F. L. Quing, and W. Y. Huang, *J Org Chem*, 1991, 2801–2804 and W. Y. Huang, *Journal of Fluorine Chemistry*, 58, 1992, 1–8. Several reagent systems have been developed for use in this reaction, such as sulfite plus an oxidant, hydroxymethane sulfinate, thiourea dioxide and sodium dithionite. The use of sodium dithionite as dehalogenating and sulfinating reagent has also been reported by W. Y. Huang, B. N. Huang and W. Wang in *Acta Chim. Sinica* (*Engl. Ed.*), 1986, 178–184, and *Acta Chim. Sinica* (*Engl. Ed.*), 1986, 68–72. The later publication discloses that the reaction with an aqueous solution of the sodium dithionite is too slow for reactions involving water-insoluble perfluoroalkyl bromides, and that cosolvents are needed to improve the mutual solubility of the various reactants and permit completion of the reaction within 30 to 35 hours. Mentioned cosolvents include acetonitrile, glycol and diethyleneglycol.

F. H. Wu and B. N. Huang, *Journal of Fluorine Chem*, 67, 1994, 233–234 reported that if DMF, acetonitrile or alcohols are used as cosolvent, both polyfluoroalkyl iodides and polyfluoroalkyl bromides will react with sodium disulfite in neutral aqueous solution to give the corresponding sulfinates in good yield. In a similar manner, $CF_3CCl_3$ reacts with sodium disulfite to give the corresponding sodium sulfinate. A disadvantage of preparing fluorinated sulfinates starting from the corresponding fluorinated iodide or bromide is that the resulting reaction product contains a large amount of by-products, particularly, inorganic salts which typically must be removed from the sulfinate.

U.S. Pat. No. 3,420,877 describes an alternative process for the preparation of fluorocarbon sulfinates. The preparation involves reacting perfluoroalkyl sulfonyl fluoride with an alkali metal sulfite or alkaline earth sulfite in an aqueous medium containing from about 10 to about 50 weight percent of a dissolved polar, inert organic solvent selected from the group consisting of dioxane, dimethoxyethane, di-n-butyl ether, tetrahydrofuran, and diethylene glycol diethyl ether. This process generally does not result in large amounts of salts that need to be removed from the resultant product, but requires use of a cosolvent that may be toxic and may have a negative impact on processes in which the sulfinate is ultimately employed, e.g., free-radical polymerization reactions.

Accordingly, there continues to be a need for an improved process for preparing fluorinated sulfinates that does not require the use of toxic solvents and preferably does not require further processing or purification of the resulting reaction mixture. It is further desirable to improve the yield of the fluorinated sulfinate.

SUMMARY OF THE INVENTION

The invention provides a process for preparing a fluorinated sulfinate product which comprises the steps of:

a) providing a reaction mixture comprising:
  (1) water;
  (2) dehalogenating and sulfinating reagent; and
  (3) fluoroaliphatic sulfonyl fluoride represented by the formula (I): $R_f$—$[SO_2F]_n$            (I)

wherein:
  $R_f$ represents a fluoroaliphatic group, and
  n is a number of 1 to 4, and typically is 1 or 2; and
  (4) at least one of the materials selected from the group consisting of (i) fluorinated surfactant, and (ii) organic cosolvent comprising, as the major component by weight of the organic solvent, alcohol having a boiling point of less than 110° C. at 760 torr;

b) heating the reaction mixture to a temperature between about 50° C. and 100° C. until the desired product yield is achieved; and c) where the organic cosolvent is employed in the reaction, optionally removing residual organic cosolvent from the resultant reaction mixture to achieve the desired level of product purity.

In a preferred embodiment, the invention provides a process for preparing a fluorinated sulfinate product comprising reacting in water, at a temperature between about 50° C. and 100° C.: (a) the fluoroaliphatic sulfonyl fluoride represented by formula (I) described above; with (b) a dehalogenating and sulfinating reagent; in the presence of the fluorinated surfactant, and without organic cosolvent until the desired yield of the product is achieved.

In another aspect, the invention provides a method of using the fluorinated sulfinate product obtained by the above-described processes as an initiation system for a free radical polymerization process.

In a preferred embodiment, the method may be used to prepare fluorine-containing polymers and comprises polymerizing, under free radical conditions, an aqueous emulsion or suspension of a polymerizable mixture containing the fluorinated sulfinate product and an oxidizing agent capable of oxidizing said tne fluorinated sulfinate compounds in the fluorinated sulfinate product to their corresponding sulfonyl radicals.

The invention provides a process for the preparation of fluorinated sulfinates using fluoroaliphatic sulfonyl fluoride that reduces or eliminates the need for organic cosolvents (such as dioxane, acetonitrile or 1,2-dimethyoxyethane) that may be toxic and/or interfere in reactions in which the fluorinated sulfinate product is used as a precursor, intermediate or initiator thereby eliminating or reducing the need for subsequent purification of the fluorinated sulfinate product. The invention accomplishes this improvement while providing comparable or improved yields to prior art processes.

DETAILED DESCRIPTION

Organic cosolvent may be used in the process either with or without fluorinated surfactant. The invention also includes reactions which do not use any organic cosolvent and employ only the fluorinated surfactant. The fluorosulfinate product largely comprises the fluorosulfinate derivatives of the fluoroaliphatic sulfonyl fluoride(s) used in the reaction mixture. Typically, the fluorosulfinate product will comprise at least about 50 weight percent and preferably at least about 70 or 80 weight percent fluorosulfinate compounds, based on the total weight of the fluorosulfinate product. The balance of the composition of the fluorosulfinate product is largely constituted of the sulfonate derivatives of the fluoroaliphatic sulfonyl fluoride(s) used to prepare the reaction mixture.

Representative fluoroaliphatic sulfinates that can be obtained with the process of the invention include the following:
$CF_3SO_2Na$
$C_8F_{17}SO_2Na$
$CF_3C(Cl)_2CF_2SO_2K$
$Cl(CF_2)_8OC_2F_4SO_2Na$
$NaO_2SC_8F_{16}SO_2Na$
$NaO_2SC_6F_{12}SO_2Na$
$NaO_2SC_2F_4OC_2F_4SO_2Na$
$NaO_2SC_2F_4OC_2F_4X$, where X is Br or I
$(CF_3)_2NCF_2CF_2SO_2Na$
$(C_2F_5)_2NCF_2CF_2SO_2Na$
$C_4F_9SO_2Na$
$C_6F_{13}SO_2Na$.

The fluoroaliphatic sulfonyl fluorides useful in the invention may be represented by formula (I). The fluoroaliphatic sulfonyl fluoride may comprise a single fluoroaliphatic sulfonyl fluoride compound or a mixture of such compounds. The fluoroaliphatic radical, $R_f$, is a mono, or polyvalent (as provided in formula (I)), fluorinated, stable, inert, non-polar and saturated moiety. It can be straight chain, branched chain, and, if sufficiently large, cyclic, or combinations thereof, such as alkyl cycloaliphatic radicals. Generally, Rf will have about 1 to 20 carbon atoms, and preferably 3 to 10, and will contain about 40 to 78 weight percent fluorine, and preferably 50 to 78 weight percent fluorine. The preferred compounds are those in which the $R_f$ radical is fully or substantially completely fluorinated, as in the case where $R_f$ is perfluoroalkyl, $C_nF_{2n+1}$—, and n is 1 to 20. The skeletal chain of the fluoroaliphatic radical consists of carbon atoms and can be interrupted by divalent oxygen, hexavalent sulfur or trivalent nitrogen hetero atoms, each of which is bonded only to carbon atoms. However, where such hetero atoms are present it is preferred that the skeletal chain does not contain more than one hetero atom for every two carbon atoms. Where $R_f$ is or contains a cyclic structure, the structure preferably has 6 ring member atoms, 1 or 2 of which can be hetero atoms, e.g., oxygen and/or nitrogen. Representative examples of $R_f$ radicals include fluorinated alkyl radicals, e.g., $C_4F_9$—, $C_6F_{13}$—, $C_8F_{17}$—, and alkoxyalkyl radicals such as, $C_3F_7OCF_2$—.

The organic cosolvent comprises, as the major component by weight of the cosolvent, one or more alcohols having a boiling point of less than 110° C. at 760 torr. In the context of this invention, the term "major component" means at least about 50 weight percent of the organic cosolvent. Preferably, the organic cosolvent will comprise at least about 90 weight percent alcohol, more preferably at least about 99 weight percent alcohol, and most preferably will consist only of alcohol. Where the organic cosolvent does not consist only of alcohol, the remaining portion of the cosolvent can be constituted of any organic solvents suitable for use as a cosolvent to prepare fluorosulfinate compounds in aqueous reaction media. Many such organic solvents are described in the prior art. Lower alkanols, particularly those having between about 1 to 4 carbon atoms, are preferred for use in the process as organic cosolvents. Examples of useful alcohols include methanol, ethanol, isopropanol, n-butanol, tertiary butanol and isobutanol. Particularly preferred alcohols are ethanol and isopropanol. If the process is carried out in the presence of organic cosolvent, regardless of its alcohol content, the organic cosolvent will preferably be removed after completion of the reaction to achieve the desired level of fluorosulfinate product purity. Any conventional method may be used to remove the organic cosolvent, such as distillation under reduced pressure.

In a more preferred embodiment of the invention, the process is carried out in the presence of a fluorinated surfactant without any organic cosolvent. In this embodiment, it will not be necessary to remove organic cosolvent from the fluorinated sulfinate product after completion of the reaction, and the resulting product may be used directly as an initiator in free radical polymerization processes without further purification. Moreover, where the fluorinated sulfinate product is intended for use in an initiation system in an emulsion or suspension polymerization process, the fluorinated surfactant used to make the fluorosulfinate product can be the same as the fluorinated surfactant employed in the polymerization process, thereby providing additional polymerization reaction efficiencies. However, it is preferred not to select a fluorinated surfactant which is the same as the fluorosulfonate derivative of the fluoroaliphatic sulfonyl fluoride (i.e., $R_f$—$[SO_3X]_n$, where n is as defined above and X is a cation such as Na) used in the reaction mixture.

Also, the fluorinated surfactant preferably will be present in the reaction mixture prior to heating the reaction mixture to ensure that the fluorinated surfactant is present from the beginning of the reaction to make the fluorinated sulfinate product.

Representative fluorinated surfactant useful in the invention may be represented by formula (II):

$$R^1_f\text{—}Q\text{—}Z \qquad (II)$$

wherein:
   $R^1_f$ represents a fluoroaliphatic group,
   Q represents an organic linking group or a covalent bond, and
   Z represents an ionic group or a water solubilizing group containing a poly(oxyalkylene) group.

Examples of ionic Z groups include groups having the formula, T-X, where the T, the surfactant polar moiety, is linked via Q to $R^1_f$, and X is a counterion to T. Examples T-X groups include those wherein T is a carboxylate group (such as ammonium carboxylates, sodium carboxylates and potassium carboxylates), those wherein T is a sulfonate group (such as ammonium sulfonates, sodium sulfonates and potassium sulfonates) and those wherein T is an ammonium group (such as in ammonium chlorides and ammonium iodides). Z can also be a water solubilizing group containing a poly(oxyalkylene) group, (OR')s, where R' preferably is an alkylene group having 2 to 4 carbon atoms, such as —CH$_2$CH$_2$—, —CH$_2$CH$_2$CH$_2$—, —CH(CH$_3$)CH$_2$—, and —CH(CH$_3$)CH(CH$_3$)— or mixtures thereof, and s preferably is a number from about 4 to about 25, and more preferably from about 6 to 20. The oxyalkylene units in the poly(oxyalkylene) group may be the same, as in poly(oxypropylene), or present as a mixture, such as in a heteric straight or branched chain of randomly distributed oxyethylene and oxypropylene units (e.g., poly(oxyethylene-co-oxypropylene)), or as in a straight or branched chain of blocks of oxyethylene units and blocks of oxypropylene units. The poly(oxyalkylene) chain can be interrupted by or include one or more catenary linkages, providing such linkages do not substantially alter the water-solubilizing character of the Z-group. The Z group may terminate with a hydrogen or a lower alkyl ether. Most preferably, Z represents an ionic group T-X wherein T represents an anion.

$R^1_f$ is a fluoroaliphatic group and is typically a fluorinated, stable, inert, non-polar, saturated moiety. Examples of suitable $R^1_f$ moieties are those present in the compounds described below. Preferably, $R^1_f$ contains at least 5 carbons and most preferably, $R^1_f$ is a perfluorinated group. Specific examples of fluorinated surfactants useful in the invention include:

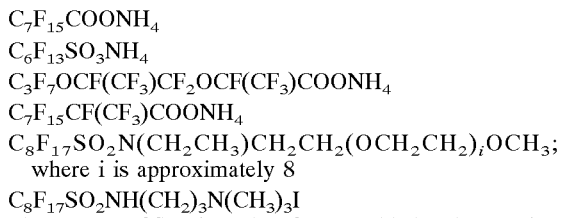

The amount of fluorinated surfactant added to the reaction mixture is not particularly critical. Preferably, the amount of fluorinated surfactant used will be between about 0.01 to 10% by weight of the total amount of fluoroaliphatic sulfonyl fluoride used to prepare the reaction mixture. If less than about 0.01% of the surfactant is employed in the reaction, the reaction will be very slow, particularly at the beginning. If more than about 10% of the surfactant is used, foaming of the reaction mixture may occur.

Examples of dehalogenating and sulfinating agents which are useful in the invention include those known in the art such as inorganic sulfites (e.g., alkali metal sulfites and earth alkali metal sulfites), inorganic dithionites (e.g., sodium dithionite and potassium dithionite) and hydrazine and certain metals, such as zinc. Particularly preferred dehalogenating and sulfinating agents are alkali metal sulfites or alkaline earth metal sulfites and specific examples of such sulfites include sodium sulfite and potassium sulfite.

The reaction may further be carried out in the presence of fluoride capturing agents such as an inorganic hydroxide, carbonate or bicarbonate compounds. Particularly useful fluoride capturing agents include alkali metal and alkaline earth metal carbonates or bicarbonates.

The reaction is carried out at a temperature between about 50° C. and 100° C. At temperatures below 50° C., the reaction will be slow whereas at a too high temperature, decomposition of the sulfinates in the product may occur. A preferred temperature range is between 55° C. and 85° C. and more preferably between 60° C. and 80° C.

The fluorinated sulfinate products prepared in accordance with the process of this invention are particularly suitable for initiating a free radical polymerization of ethylenically unsaturated monomers. Preferably, the fluorinated sulfinate products are used to initiate the homo- or copolymerization of polymerizable mixtures comprising fluorine-containing ethylenically unsaturated monomer, and optionally, fluorine-free, terminally unsaturated monoolefin comonomers (e.g., ethylene or propylene), or iodine- or bromine-containing cure-site comonomers. The polymerization technique used is typically an emulsion or suspension polymerization in an aqueous medium.

Examples of fluorine-containing ethylenically unsaturated monomers include the terminally unsaturated monoolefins typically used for the preparation of fluorine-containing polymers such as vinylidene fluoride, hexafluoropropene, chlorotrifluoroethylene, 2-chloropentafluoropropene, perfluoroalkyl vinyl ethers (e.g., CF$_3$OCF=CF$_2$ or CF$_3$CF$_2$OCF=CF$_2$), tetrafluoroethylene, 1-hydropentafluoropropene, 2-hydropentafluoropropene, dichlorodifluoroethylene, trifluoroethylene, 1,1-dichlorofluoroethylene, vinyl fluoride, and mixtures thereof. Perfluoro-1,3-dioxoles may also be used. The perfluoro-1,3-dioxole monomers and their copolymers are described, for example, in U.S. Pat. No. 4,558,141 (Squire). Certain fluorine-containing di-olefins are also useful, such as, perfluorodiallylether and perfluoro-1,3-butadiene.

Examples of iodine- or bromine-containing cure-site comonomers include those known in the art for the preparation of peroxide-curable polymers, e.g., peroxide-curable fluoroelastomers. Suitable cure-site monomers include terminally unsaturated monoolefins having about 2 to 4 carbon atoms such as bromodifluoroethylene, bromotrifluoroethylene, iodotrifluoroethylene, and 4-bromo-3,3,4,4-tetrafluorobutene-1.

The fluorine-containing monomer may also be copolymerized with fluorine-free terminally unsaturated monoolefin comonomers, e.g., ethylene or propylene. However, preferably at least 5% by weight, and most preferably at least 50%, of all monomers in the polymerizable mixture are fluorine-containing. Preferably, all or essentially all of the comonomers in the polymerizable mixture are ethylenically unsaturated monomers.

The initiation of a free radical polymerization in accordance with the invention uses the fluorinated sulfinate product as a reducing agent and a water-soluble oxidizing agent capable of converting the sulfinate compounds in the product to their corresponding sulfonyl radicals. Preferred oxidizing agents are sodium, potassium, and ammonium persulfates, perphosphates, perborates, and percarbonates. Particularly preferred oxidizing agents are sodium, potassium, and ammonium persulfates. Still further suitable oxidizing agents include water-soluble oxidizing agents containing a chlorate ion, a bromate ion or a hypochlorite ion. The sulfonyl radical so produced is believed to eliminate SO$_2$, forming a fluorinated radical that initiates the polymerization of the ethylenically unsaturated monomers.

In addition to the fluorosulfinate product, other reducing agents can be present in the polymerizable mixture, such as sodium, potassium or ammonium sulfites, bisulfite, metabisulfite, hyposulfite, thiosulfite, phosphite and sodium or potassium formaldehyde sulfoxylate or hypophosphite. Activators such as ferrous, cuprous, and silver salts, may also be present.

Aqueous emulsion polymerizations can be carried out under conventional steady-state conditions in which, for example, monomers, water, surfactants, buffers and catalysts are fed continuously to a stirred reactor under optimum pressure and temperature conditions while the resulting emulsion or suspension is removed continuously. An alternative technique is batch or semi-batch polymerization by feeding the ingredients into a stirred reactor and allowing them to react at a set temperature for a specified length of time or by charging ingredients into the reactor and feeding the monomer into the reactor to maintain a constant pressure until a desired amount of polymer is formed.

The amount of fluoroaliphatic sulfinate product used in such polymerization reactions can vary, depending, for example, on the molecular weight of polymer desired. Preferably the amount of fluoroaliphatic sulfinate product used is from about 0.01 to 50 mole %, and most preferably 0.05 to 10 mole %, based on total quantity of monomer in the polymerizable mixture.

Combinations of monosulfinates, disulfinates, and trisulfinates can be used, depending on whether it is desired to use sulfinate as an initiator, a monomer, or both. When polyvalent sulfinates are used, the sulfinate segment is incorporated into the polymer backbone. When monosulfinates are used, the fluorinated moiety is incorporated as a polymer end group.

The invention is further illustrated by the following examples without the intention to limit the invention thereto. All parts are by weight unless otherwise indicated.

EXAMPLES

Analysis

GLC-analysis was performed using a wall-coated, open-tubular (WCOT) fused silica colurnn, 30 m×0.25 mm×0.25 μm, with a 95% dimethylsiloxane and 5% diphenylsiloxane phase, (HP-5), available from Hewlett Packard $^{19}$F NMR analysis was performed using a Bruker AC (alternating current), 300 Hz apparatus.

List of Abbreviations, Trademark and Tradenames Used in the Examples and Comparative Examples
DI-water: deionized water
EtOH: ethyl alcohol
$C_4F_9SO_2F$: perfluorobutyl sulfonyl fluoride
$C_4F_9SO_2Na$: sodium perfluorobutyl sulfinate
$C_8F_{17}SO_2F$: perfluorooctyl sulfonyl fluoride
$C_8F_{17}SO_2Na$: sodium perfluorooctyl sulfinate
$C_8F_{17}SO_3Na$: sodium perfluorooctyl sulfonate
$Na_2SO_3$: sodium sulfite
$NaHCO_3$: sodium bicarbonate
FC-100: a fluorochemical amphoteric surfactant, commercially available from 3M Co., St. Paul, Minn.

Examples 1 to 5 and Comparative Example C-1

In Example 1, sodium perfluorobutyl sulfinate was prepared as follows:

A three necked 500 ml reaction flask, equipped with a reflux condenser, a stirrer, a thermometer and a heating mantle was charged with 30.2 g of $C_4F_9SO_2F$ (0.1 moles), 15.1 g $Na_2SO_3$ (0.12 moles), 16.8 g $NaHCO_3$ (0.2 moles), 50 g EtOH and 50 g DI-water. The reaction mixture was degassed 3 times using nitrogen and aspirator vacuum. The mixture was then heated to 60° C. under a nitrogen atmosphere for 16 hours. A slightly yellow reaction mixture with a pH of 6.5 was obtained. EtOH was stripped off under reduced pressure using an aspirator vacuum (20 torr and temperature between 60–85° C.) and the temperature was kept below 110° C. in order to avoid thermal decomposition of the sulfinate product. $^{19}$F analysis indicated a yield of 65% sodium perfluorobutyl sulfinate and 25% sodium perfluorobutyl sulfonate.

Examples 2 to 5 and Comparative Example C-1 were prepared using essentially the same procedure used in Example 1, except that the reaction media described in Table 1 were employed in the reactions.

TABLE 1

Synthesis of Sodium Perfluorobutyl Sulfinate

| Ex No | Reaction medium | Additives |
|---|---|---|
| 1 | EtOH/DI-water 50/50 | $Na_2SO_3$ (0.12 moles) + $NaHCO_3$ (0.2 moles) |
| 2 | EtOH/DI-water 50/50 | NaOH (0.1 moles) + $NaHCO_3$ (0.1 moles) |
| 3 | EtOH/DI-water 50/50 | $Na_2SO_3$ (0.22 moles) ($^1$) |
| 4 | Isopropanol/DI-water 50/50 | $Na_2SO_3$ (0.12 moles) + $NaHCO_3$ (0.2 moles) |
| 5 | EtOH/DI-water 150/50 | $Na_2SO_3$ (0.12 moles) + $NaHCO_3$ (0.2 moles) |
| C-1 | Dioxane/DI-water 50/50 | $Na_2SO_3$ (0.12 moles) + $NaHCO_3$ (0.2 moles) |

Note:
($^1$) No additional base was added to the reaction mixture; pH of the solution after completion of the reaction was about 2.

$^{19}$F NMR analysis indicated of the reactions products of the Examples 1–5 reaction mixtures contained about 65% of sodium perfluorobutyl sulfinate and about 25% of sodium perfluorobutyl sulfonate. GLC analysis indicated that the amount of residual alcohol in the reaction products after evaporation was less than 1 wt.%. In Comparative Example C-1, a reaction product containing about 65% sodium perfluorobutyl sulfinate and about 30% sodium perfluorobutyl sulfonate was formed and the reaction product contained about 1% residual dioxane after evaporation.

Examples 6 to 9 and Comparative Example C-2

In Examples 6 to 9, sodium perfluorooctyl sulfinate was made according to the procedure described above for Examples 1 to 5 except that the alcohols listed in Table 2 were used. Comparative Example C-2 was made using dioxane as the organic cosolvent. After the reaction, the alcohol (or dioxane in C-2) was removed under reduced pressure (aspirator vacuum) at a temperature between 60–85° C.

$^{19}$F NMR analysis was used to determine the amount of sodium perfluorooctyl sulfinate and sodium perfluorooctylsulfonate that formed during the reaction. The results are given in Table 2.

TABLE 2

Reaction Medium and Yield of Sodium Perfluorooctyl Sulfinate

| Ex No | Reaction medium | Yield of $C_8F_{17}SO_2Na$ | Yield of $C_8F_{17}SO_3Na$ |
|---|---|---|---|
| 6 | EtOH | 70% | 28% |
| 7 | Isobutanol | 62% | 35% |
| 8 | Isopropanol | 65% | 31% |
| 9 | Tertiary butyl alcohol | 66% | 30% |
| C-2 | Dioxane | 68% | 32% |

The data in Table 2 shows that other alcohols may be used in the invention as organic cosolvents in the synthesis of sodium perfluorocarbon sulfinates. The data also shows that the yields of sodium perfluorocarbon sulfinates and perfluorocarbon sulfonates were relatively unaffected by the alcohol used in the reaction.

Examples 10 to 21 and Comparative Example C-3

Example 10 illustrates the preparation of sodium perfluorooctyl sulfinate using a fluorinated surfactant, $C_7F_{15}COO$ $^-NH_4^+$. No alcohol or other organic cosolvent was used in combination with deionized water.

A three necked 500 ml reaction flask, equipped with a reflux condenser, a stirrer, a thermometer and a heating mantle was charged with 50.2 g (0.1 moles) $C_8F_{17}SO_2F$, 15.1 g (0.12 moles) $Na_2SO_3$, 16.8 g (0.2 moles) $NaHCO_3$, 2.5 g $C_7F_{15}COO^-NH_4^+$ and 200 g DI-water. After degassing 3 times with nitrogen and aspirator vacuum, the reaction was run at 70° C. for 16 hours under a nitrogen atmosphere. A slightly yellow mixture was obtained having a pH of about 6.5.

$^{19}$F-NMR analysis indicated that the reaction product contained about 80% $C_8F_{17}SO_2Na$ and about 10% $C_8F_{17}SO_3Na$. Traces of monohydrofluorooctane were also detected.

Examples 11 to 21 were prepared essentially according to the same procedure as Example 10 except that the ingredients listed in Table 3 were used. Comparative Example C-3 was prepared using 100 g each of dioxane and water, without addition of fluorinated surfactant.

TABLE 3

Composition and Reaction Medium of Fluorinated Sulfinates

| Ex No | Fluorosulfonyl Fluoride Reactant | Fluorinated Surfactant | Yield |
|---|---|---|---|
| 11 | $C_4F_9SO_2F$ | $C_7F_{15}COO^-NH_4^+$ | 82 |
| 12 | $C_6F_{13}SO_2F$ | $C_7F_{15}COO^-NH_4^+$ | 74 |
| 13 | $FO_2S(CF_2)_4SO_2F$ | $C_7F_{15}COO^-NH_4^+$ | 76 ($^2$) |
| 14 | $C_4F_9SO_2F$ ($^3$) | $C_7F_{15}COO^-NH_4^+$ | 70 |
| 15 | $C_4F_9SO_2F$ ($^4$) | $C_7F_{15}COO^-NH_4^+$ | 76 |
| 16 | $C_4F_9SO_2F$ | $C_6F_{13}SO_3^-NH_4^+$ | 75 |
| 17 | $C_8F_{17}SO_2F$ | $C_3F_7OCF(CF_3)CF_2OCF(CF_3)COO^-NH_4^+$ | 82 |
| 18 | $C_8F_{17}SO_2F$ | $C_7F_{15}CF(CF_3)COO^-NH_4^+$ | 85 |
| 19 | $C_4F_9SO_2F$ | $C_8F_{17}SO_2N(CH_2CH_3)CH_2CH_2(OCH_2CH_2)_nOCH_3$; where n is approximately 8 | 78 |
| 20 | $C_4F_9SO_2F$ | FC-100 | 72 |
| 21 | $C_4F_9SO_2F$ | $C_8F_{17}SO_2NH(CH_2)_3N^+(CH_3)_3I^-$ | 72 |
| C-3 | $C_8F_{17}SO_2F$ | — | 66 |

Notes:
($^2$) Sum of mono and disulfinate product present.
($^3$) 0.1 moles of NaOH and 0.1 moles $NaHCO_3$ were used in the reaction instead of 0.12 moles of $Na_2SO_3$ and 0.2 moles $NaHCO_3$.
($^4$) 0.22 moles of $Na_2SO_3$ and no additional base were used in the reaction. pH of reaction mixture after completion of the reaction was about 2.

The results in Table 3 indicate that the use of fluorinated surfactant in the reaction medium resulted in an increased yield of sodium perfluorocarbon sulfinate in the fluorosulfinate product.

A major advantage of the process to make sodium perfluorocarbon sulfinates using fluorinated surfactant is that organic solvents can be avoided in the reaction product that will interfere with the reactions in which the sulfinates may be used as intermediates, precursors or initiators. The fluorinated surfactants useful in this invention can be selected from those surfactants which will not interfere in a free radical polymerization process.

I claim:

1. A process for preparing a fluorinated sulfinate product comprising the steps of:

a) providing a reaction mixture comprising:
 (1) water;
 (2) dehalogenating and sulfinating reagent;
 (3) fluoroaliphatic sulfonyl fluoride represented by the formula:

$R_f$—[$SO_2F$]$_n$ wherein:
 $R_f$ is a fluoroaliphatic group, and
 n is a number from about 1 to 4; and
 (4) at least one material selected from the group consisting of:
 (i) fluorinated surfactant, and
 (ii) organic cosolvent comprising, as the major component by weight, alcohol having a boiling point of less than 110° C. at 760 torr; and b) heating the reaction mixture to a temperature between 50° C. and 100° C. until the desired product yield is achieved.

2. A process according to claim 1 wherein the reaction mixture consists essentially of the water, the dehalogenating and sulfinating reagent, the fluoroaliphatic sulfonyl fluoride, and at least one material selected from the group consisting of: (1) the fluorinated surfactant, and (2) the organic cosolvent.

3. A process according to claim 2 wherein the reaction mixture further contains fluoride capturing agent.

4. A process according to claim 1 wherein the reaction mixture consists of the water, the dehalogenating and sulfinating reagent, the fluoroaliphatic sulfonyl fluoride, and at least one material selected from the group consisting of: (1) the fluorinated surfactant, and (2) the organic cosolvent.

5. A process according to claim 4 wherein the reaction mixture further contains fluoride capturing agent.

6. A process according to claim 1 wherein the alcohol is a lower alkanol having about 1 to 4 carbon atoms.

7. A process according to claim 1 to wherein the organic cosolvent comprises at least about 99 weight percent of the alcohol.

8. A process according to any of claim 1 wherein the organic cosolvent consists essentially of alcohol.

9. A process according to claim 1 wherein the organic cosolvent consists of alcohol.

10. A process according to claim 1 wherein the reaction mixture comprises fluorinated surfactant and the amount of the surfactant used to prepare the reaction mixture is between about 0.01% to 10% by weight fluoroaliphatic sulfonyl fluoride used to prepare the reaction mixture.

11. A process according to claim 1 wherein the fluorinated surfactant is represented by the following formula:

wherein:
  $R^1_f$ represents a fluoroaliphatic radical,
  Q represents an organic linking group or a covalent bond, and
  Z represents an ionic group or a water solubilizing group containing a poly(oxyalkylene) group.

12. A process according to claim 1 wherein the fluorinated surfactant is an anionic fluorinated surfactant.

13. A process according to claim 12 wherein said fluorinated surfactant comprises $C_7F_{15}COONH_4$.

14. A process according to claim 1 wherein the material of item (4) is the fluorinated surfactant alone.

15. A process according to claim 1 wherein the material of item (4) is only organic cosolvent.

16. A process according to claim 1 wherein the process comprises the additional step of removing residual organic cosolvent from the fluorosulfinate product until the desired product purity is achieved.

17. A process according to claim 1 wherein the $R_f$ in the fluoroaliphatic sulfonyl fluoride contains about 3 to 10 carbon atoms.

18. A process for preparing a fluorinated sulfinate product comprising, reacting in water a fluoroaliphatic sulfonyl fluoride represented by the following formula:

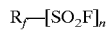

wherein:

$R_f$ represents a fluoroaliphatic group, and n is a number from about 1 to 4; with a dehalogenating and sulfinating reagent at a temperature between 50° C. and 100° C. in the presence of fluorinated surfactant, and without organic cosolvent other than an alcohol, until the desired yield of product has been achieved.

19. A process according to claim 18 wherein fluorinated surfactant has a structure different than the sulfonate derivative of the fluoroaliphatic sulfonyl fluoride.

20. A process according to claim 1 wherein said dehalogenating and sulfinating reagent is selected from the group consisting of inorganic sulfites, inorganic dithionites, hydrazine, and zinc.

21. A process according to claim 3 wherein said fluoride capturing agent is selected from the group consisting of inorganic hydroxide, carbonate, and bicarbonate compounds.

* * * * *

UNITED STATES PATENT AND TRADEMARK OFFICE
CERTIFICATE OF CORRECTION

PATENT NO. : 6,462,228 B1 Page 1 of 1
DATED : October 8, 2002
INVENTOR(S) : Dams, Rudolf J.

It is certified that error appears in the above-identified patent and that said Letters Patent is hereby corrected as shown below:

<u>Title page,</u>
Item [57], ABSTRACT,
Line 3, "reagent:" should read -- reagent; --

Item [56], OTHER PUBLICATIONS,
10th reference, "Ruldolf" should read -- Rudolf --
11th reference, "Ruldolf" should read -- Rudolf --
24th reference, "*FLuorine*" should read -- *Fluorine* --
25th reference, "ChangMing" should read -- Chang-Ming --

<u>Column 2,</u>
Line 65, "tne" should read -- the --

<u>Column 10,</u>
Line 58, "according to any claim 1" should read -- according to claim 1 --

Signed and Sealed this

Twenty-sixth Day of August, 2003

JAMES E. ROGAN
*Director of the United States Patent and Trademark Office*